United States Patent
Mao et al.

(10) Patent No.: US 12,215,393 B2
(45) Date of Patent: Feb. 4, 2025

(54) METHOD AND APPLICATION FOR RAPID AND ACCURATE CHROMOSOMAL LOCATION OF ECONOMIC TRAITS IN LAVER

(71) Applicants: Ocean University of China, Qingdao (CN); Hainan Tropical Ocean University, Hainan (CN)

(72) Inventors: Yunxiang Mao, Qingdao (CN); Xinzi Yu, Qingdao (CN); Fanna Kong, Qingdao (CN); Min Cao, Qingdao (CN)

(73) Assignees: Ocean University of China, Qingdao (CN); Hainan Tropical Ocean University, Hainan (CN)

( * ) Notice: Subject to any disclaimer, the term of this patent is extended or adjusted under 35 U.S.C. 154(b) by 871 days.

(21) Appl. No.: 17/185,866

(22) Filed: Feb. 25, 2021

(65) Prior Publication Data

US 2021/0269887 A1    Sep. 2, 2021

(30) Foreign Application Priority Data

Feb. 27, 2020 (CN) .......................... 202010122553.X

(51) Int. Cl.
*C12Q 1/6895* (2018.01)
*C12Q 1/6827* (2018.01)
*C12Q 1/686* (2018.01)

(52) U.S. Cl.
CPC ......... *C12Q 1/6895* (2013.01); *C12Q 1/6827* (2013.01); *C12Q 1/686* (2013.01)

(58) Field of Classification Search
CPC ..... C12Q 1/6895; C12Q 1/6827; C12Q 1/686
See application file for complete search history.

(56) References Cited

PUBLICATIONS

Takahashi M, Mikami K. Oxidative Stress Promotes Asexual Reproduction and Apogamy in the Red Seaweed *Pyropia yezoensis*. Front Plant Sci. Jan. 27, 2017;8:62. doi: 10.3389/fpls.2017.00062. PMID: 28191011; PMCID: PMC5270553 (Year: 2017).*

Warden et al. Detailed comparison of two popular variant calling packages for exome and targeted exon studies. PeerJ. Sep. 30, 2014;2:e600. doi: 10.7717/peerj.600. PMID: 25289185; PMCID: PMC4184249. (Year: 2014).*

Guo et al. Whole-genome resequencing of Xishuangbanna fighting chicken to identify signatures of selection. Genet Sel Evol 48, 62 (2016). doi.org/10.1186/s12711-016-0239-4 (Year: 2016).*

Vallejo-Marín et al. "The ecological and evolutionary consequences of clonality for plant mating." Annual Review of Ecology, Evolution, and Systematics 41 (2010): 193-213. (Year: 2010).*

Huang et al. "Construction of a genetic linkage map in Pyropia yezoensis (Bangiales, Rhodophyta) and QTL analysis of several economic traits of blades." PLoS One 14.3 (2019): e0209128 (Year: 2019).*

Luo, Huaiyong, et al. "Discovery of genomic regions and candidate genes controlling shelling percentage using QTL-seq approach in cultivated peanut (*Arachis hypogaea* L.)." Plant Biotechnology Journal 17.7 (2019): 1248-1260. (Year: 2019).*

Wen, Junqin, et al. "Identification of heat-tolerance QTLs and high-temperature stress-responsive genes through conventional QTL mapping, QTL-seq and RNA-seq in tomato." BMC plant biology 19 (2019): 1-17. (Year: 2019).*

* cited by examiner

*Primary Examiner* — Aaron A Priest
*Assistant Examiner* — Tian N Yu
(74) *Attorney, Agent, or Firm* — Bochner PLLC; Andrew Bochner; Eric Kleinertz

(57) ABSTRACT

The disclosure discloses a method and application for rapid and accurate chromosomal location of economic traits in laver, belonging to the fields of genomics and molecular breeding, wherein comprising the following steps: distinguishing the different genotype sectors by the color difference of pigment mutants, releasing monospores based on the asexual reproduction of single-genotype sectors, forming offspring CMD population; performing QTL-seq analysis on the extreme phenotype pools of offspring CMD population by SNP/InDel markers; and combining KASP and RNA-seq to predict the location of the genes of discrete traits or major QTL. The disclosure may solve the problem of difficulty in genetic analysis of various traits caused by the genotypic chimeric haploid characteristics.

9 Claims, 3 Drawing Sheets

METHOD AND APPLICATION FOR RAPID AND ACCURATE CHROMOSOMAL LOCATION OF ECONOMIC TRAITS IN LAVER

CROSS REFERENCE TO RELATED APPLICATION

This application claims the priority of Chinese Patent Application No. 202010122553.X, entitled "Method and application for rapid and accurate chromosomal location of economic traits in laver" filed with China National Intellectual Property Administration on Feb. 27, 2020, which is incorporated herein by reference in its entirety.

TECHNICAL FIELD

The disclosure belongs to the fields of genomics and molecular breeding, and in particular to a method and application for distinguishing meiotic tetrad by using pigment mutants to rapidly and accurately locate economic traits in laver.

BACKGROUND ART

The life history and generational changes of layer are very different from those of higher plants, which results in that the traditional methods of population construction for genetic analysis in higher plants are not suitable for laver. The leaves of layer are developed from conchospores (2n). During the germination of conchospores, meiosis occurs and produces haploid and ordered tetrad. Different from the process of producing a single germ cell through meiosis in animals and higher plants, the four cells (ordered tetrad (n)) produced through meiosis in layer are combined together. The genotype of each cell in the tetrad may be different due to homologous recombination during meiosis. Each cell (n) of the ordered tetrad subsequently develops into a part of the leaf sequentially through mitosis, and therefore, the leaves of layer are genotypic chimeric haploids (except for those developed from homozygous conchospores). Before the discovery of pigment mutants, the genotypic chimeric leaves developed from four cells of tetrad could not be distinguished visually, which restrict the research on the location of laver's traits. Four cells of one tetrad with different genotypes produced by homologous recombination during meiosis can be clearly distinguished by pigment mutants, and thus the single-genotype color sectors exchanged by homologous recombination are obtained. The characteristics of small biomass and incomplete leaves of single-genotype color sectors limits the measurement and sequencing of traits. The leaves of layer have the characteristics of releasing a large number of monospores based on the asexual reproduction of the layer thallus. Culturing the monospores induced and released by the single-genotype color sectors can quickly provide a large amount of material for the parallel repeated measurement of single-genotype traits.

Molecular markers are indispensable for the researches of genetic location. From the earliest RFLP to the popular SSR in previous years, the marker density has been continuously increased. When the density and uniformity of SSR and other second-generation markers can not meet the needs of breeders for genetic research such as genetic map, the third generation of molecular marker SNP came into being. The map made with SNP markers is the best quality, highest density and most uniform map under present technology. Moreover, with the reduction of sequencing costs, researchers can quickly obtain a large number of SNP markers through whole-genome resequencing based on the known genomes. The combination of SNP and other molecular markers can also greatly improve the resolution and make the use of genetic resources more effective.

QTL-seq is a method developed in recent years to use high-throughput sequencing for bulk segregant analysis (BSA) to locate the major genes of quantitative traits and the genes of discrete traits. It is suitable for offspring populations of parents with a pair of relative traits. In this method, 20-50 individuals with extreme phenotypes in a segregating mapping population are selected to form extreme phenotype progeny pools for whole gene sequencing respectively. The genome of one of the parents is used as a reference to analyze the two extreme phenotype progeny pools based on the SNPs/InDels found in the two parents, calculate the SNPs/InDels-index of each SNP in progeny pools, and predict the QTL or gene according to the distribution of SNP-index. Although QTL-seq conveniently and effectively reduces the range of candidate QTL regions, it also has many limitations, for example, the target gene may not be identified in regions with insufficient meiotic recombination events. To overcome these limitations, developing competitive allele-specific PCR (KASP) technology and RNA-seq were expected to be combined with QTL-seq to achieve rapid and fine mapping of traits of laver.

SUMMARY OF THE APPLICATION

In view of the problem that the traditional methods of population construction for genetic analysis in higher plants are not suitable for laver, the purpose of the present disclosure is to distinguish single-genotype color sectors by pigment markers, and by taking advantage of the characteristics of monospores released by layer leaves, quickly obtain a large number of single-genotype complete leaves that have undergone recombination and form a Color-sectored Monospore Developed population (CMD Population), and then combined with QTL-seq, the development of Kompetitive Allele Specific PCR (KASP) technology and RNA-seq, achieving rapid and fine mapping of traits in laver.

In order to achieve the above purpose, the present disclosure provides the following technical scheme:

A method for rapid and accurate chromosomal location of economic traits in laver, wherein including the following steps: marking and distinguishing the different genotype regions of thallus in layer developed from meiotic tetrad by the color marks of pigment mutants, inducing and releasing monospores based on the asexual reproduction of monochromatic single-genotype sectors of the leaves for obtaining complete leaves with the same genotype in batch, forming offspring Color-sectored Monospore Developed population to evaluate and measure a commonality of target genetic trait; using the wild-type parent as a reference genome and performing QTL-seq analysis on the extreme phenotype pools of offspring Color-sectored Monospore Developed population by SNP/InDel markers; and combining Kompetitive Allele Specific PCR and RNA-seq methods to predict the location of target trait genes or major QTL.

In one embodiment, forming the offspring Color-sectored Monospore Developed population including the following steps:
i. crossing wild-type×pigment mutants to obtain F1 (filial generation 1) chimeric leaves, marking and distinguishing the different genotype regions of thallus in layer developed from meiotic tetrad on the chimeric leaves by the color of pigment mutants, and each separated region (sector) is a single-genotype;

ii. inducing and releasing monospores based on the asexual reproduction of single-genotype sectors by sectioning single-genotype sector into small pieces (microthalli) that were cultivated at 15° C., and then numerous complete leaves with the single-genotype obtained, forming offspring Color-sectored Monospore Developed population to measure and analyze the genetic trait.

In one embodiment, the QTL-seq analysis including the following steps:

i. in the offspring Color-sectored Monospore Developed population of the hybrid of wild-type×pigment mutants, mixing a certain quantum of offspring Color-sectored Monospore Developed individuals according to their traits to form a pair of extreme trait offspring pool with the same individual quantity;

ii. performing whole-genome sequencing of the wild-type parents, pigment mutants and offspring pool; filtering the sequenced data, calling and filtering SNP and/or InDels and annotating SNP and/or InDels;

iii. extracting SNP/InDels which are homogenic in each parent but different between the two parents; using the genotype of the wild-type parent as a reference to calculate the Δ(SNP/InDel-index) of the offspring pool; determining the candidate genomic regions related to trait.

In one embodiment, filtering the sequenced data, calling and filtering SNP and/or InDels and annotating SNP and/or InDels including: marking repeats by Picard software; detecting single nucleotide polymorphisms and InDels by SAMtools and GATK software; the filtering standards of SNP/InDels are as follows: read depth ≥4, ≤1000; mapping quality ≥20; adjacent SNP distance ≥5 bp; annotating SNP or InDels by ANNOVER software.

In one embodiment, the number of individual quantity in each extreme trait offspring pool ≥24, and the more individuals, the better the locating.

In one embodiment, the Δ(SNP/InDel-index) is the difference between the SNP/InDel-index of each SNP/InDel in one offspring mixed pool subtracts the SNP/InDel-index of another mixed pool.

In one embodiment, the SNP/InDel-index including the following steps:

extracting SNP/InDels which are homogenic in each parent but different between the two parents; using the genotype of the wild-type parent as a reference to count the number of variabel reads of pigment-mutant parent mutation in offspring pool and calculate the ratio of the number of reads to the total number, which is the SNP/InDel-index of each SNP/InDel sites.

In another embodiment, the method for rapid and accurate chromosomal location of economic traits in layer is used in fine mapping to identify the functional genetic locus for red coloration in *Pyropia yezoensis* thallus, wherein including the following steps: analyzing the wild-type mixed pool and the red mutant mixed pool of the offspring Color-sectored Monospore Developed population of the cross combination of wild-type RZ×red mutant HT by QTL-seq, which may locate the red trait locus of the layer leaf within 4.9 Mb; further narrowing the candidate interval to 1.42 Mb by Kompetitive Allele Specific PCR; combining with RNA-seq method to determine the potential candidate gene for controlling red coloring in HT is Py08429.

The advantages of the embodiments of the present disclosure are as follows:

The pigment mutants represented by the red mutant are a good visual marker for distinguishing the chimeric genotypes on the offspring leaves of the hybrid. Red color markers or other pigment mutant color markers are used to distinguish the chimeric genotypes of hybrid offspring leaves. The Color-sectored Monospore Developed population is quickly constructed, and the required traits are measured and evaluated. The pair of extreme phenotypic offspring pools composed of the Color-sectored Monospore Developed population individuals of the wild-type×pigment mutant hybrid is analyzed by the combination methods of QTL-seq, Kompetitive Allele Specific PCR and RNA-seq. The present disclosure provides new research ideas for the location of genetic traits in layer and Bangiates species.

Taking the screening of disease resistance traits as an example, the single-genotype sectors of the leaf developed from the tetrad may be easily distinguished by crossing a normal non-resistant disease-resistant pigment mutant with a disease-resistant wild-type strain, and then the Color-sectored Monospore Developed population is obtained. Then the disease resistance levels of different Color-sectored Monospore Developed individuals are evaluated, and the individuals with extreme disease-resistance phenotype and non-resistant disease-resistant phenotype among these Color-sectored Monospore Developed individuals are subjected to a mixed DNA pool analysis to screen for disease resistance candidate genes. Therefore, in the examples of the present disclosure, the Color-sectored Monospore Developed population obtained from the F1 (filial generation 1) through the crossing experiment between red mutation and wild type is used to determine and locate candidate genes for red coloration traits, which can not only deepen the understanding of red algae coloring mechanism, but also help to construct population through color marker, so as to analyze and locate other genetic traits (quantitative and discrete traits). The present disclosure lays a foundation for the subsequent use of pigment mutants for the analysis of other traits of layer and Bangiates species.

DETAILED DESCRIPTION OF THE EMBODIMENTS

Figure 1:
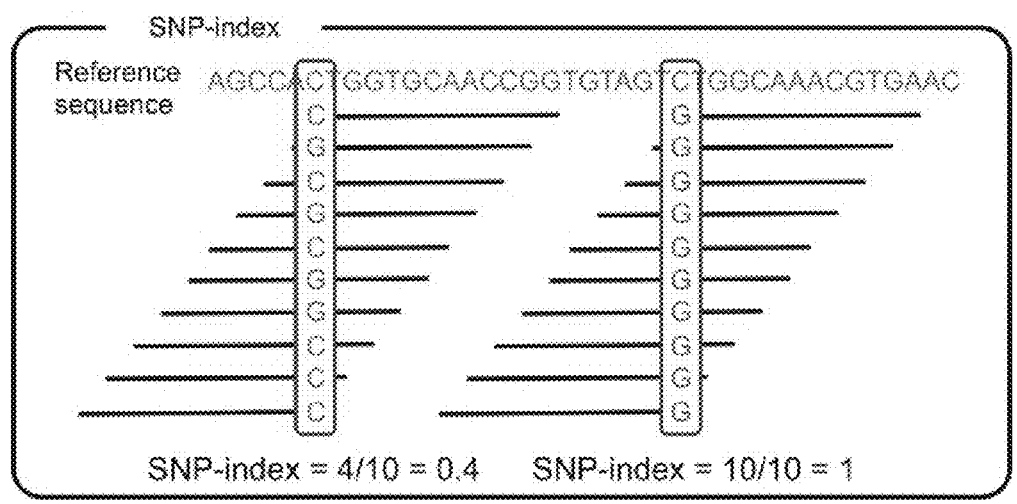
FIG. 1 is a schematic diagram of SNP/InDel-index calculation in the existing technology (Takagi, Abe et al. 2013)

Unless otherwise specified, the terms used in the present disclosure generally have the meanings commonly understood by those of ordinary skilled in the field.

The present disclosure will be further described below in combination with the examples and with reference to data. The following examples are only to illustrate the present disclosure, but the present disclosure is not limited by the specific embodiments disclosed below.

Example 1

1. Material Source

Two pure strains of *Pyropia yezoensis* cultured in the laboratory were used, namely wild-type RZ and red mutant HT. A spontaneous red mutant HT was isolated from wild-type PYL-349. Since each color sector of the offspring four-sectored chimeras and the two-terminal color sectors of the three-sectored chimeras respectively had a unified genotype, the four-sectored chimeras and the three-sectored chimeras were screened from F1 (filial generation 1) leaves (single-genotype). The Color-sectored Monospore Developed population was constructed with the above method, and its color traits were evaluated.

The test materials were two pairs of mixed pools including a pair of a red pool composed of 24 red individuals and a wild-type pool composed of 24 wild-types, and a pair of a red pool composed of 56 red individuals and a wild-type pool composed of 56 wild-types, in the Color-sectored Monospore Developed population of the hybrid combination of wild-type RZ×red mutant HT.

2. Method 2.1 Library Construction and Sequencing

Plant genomic extraction DNA kit (Tiangen, China) was used to extract DNA from the parental leaves and individual of each offspring Color-sectored Monospore Developed population. Qubit.2.0 fluorometer (Invitrogen), 1% agarose gel electrophoresis and N60 UV-Vis spectrophotometer (Implen, Munich, Germany) were used to detect the concentration and quality of DNA.

2.2 QTL-Seq

As the parent, RZ had a high quality reference genome. In order to further explore the influence of the individual number of mixed pool on the locating function, a total of five DNA libraries were constructed, namely, P1, RT24, WT24, RT56, and WT56. The P1 pool was from the blades of HT (paternal); two pairs of mixed pools RT24-WT24 and RT56-WT56 were constructed by equally mixing 24 or 56 offspring Color-sectored Monospore Developed individuals with different color traits (wild-type/WT or red-type/RT). Pair-end sequencing libraries with insert sizes of approximately 350 bp and a read length of 150 bp were subjected to whole-genome resequencing with Illumina HiSeq 2000 platform (Illumina, USA).

The raw reads obtained from the parental and four offspring libraries were filtered, and aligned to the RZ genome sequence of *P. yezoensis* using the Burrows-Wheeler alignment tool (BWA). Picard software was used to mark duplicates. SAMtools (settings: -bS-t, "rmdup") and GATK software were used to detect single nucleotide polymorphisms (SNPs) and InDels. The filtering standards of SNP/InDels were as follows: read depth ≥4, ≤1000; mapping quality ≥20; adjacent SNP distance SNP ≥5 bp; SNP or InDels were annotated by ANNOVER software.

Homozygous SNP/InDels between the two parents were extracted from the VCF file. The genotype of RZ was used as a reference to calculate the statistic read number in the offspring pools (RT24-WT24; RT56-WT56). Then, SNP/InDel-index and the Δ(SNP/InDel-index) values were calculated to identify candidate genomic regions associated with the red-type trait of HT. The principle is shown in FIG. 1. Δ(SNP/InDel-index) is the difference between the SNP/InDel-index of each SNP/InDel in the red mixed pool subtracts the SNP/InDel-index of the wild-type mixed pool. The SNP/InDel-index and Δ(SNP/InDel-index) values were calculated to determine candidate genomic regions related to the red-type traits of HT. A sliding window method with a window size of 1 Mb and a step size of 100 kb was used to calculate the average Δ (SNP/InDel-index) within a given genome interval. The Δ(SNP/InDel-index) of the RT and WT pools were plotted on a Manhattan plot. If the genomic region contains the target gene, the Δ(SNP/InDel-index) value should be significantly different from 0. The statistical confidence interval Δ(SNP/InDel-index) of all SNP positions with a given reading depth were calculated, and 95% and 99% confidence interval obtained. The region above the confidence value was defined as a candidate region associated with red coloring by detecting Δ(SNP/InDel-index).

2.3 Verification of Candidate Interval

For confirming the accuracy of candidate region identified by QTL-seq, 86 of Color-sectored Monospore Developed individuals from F1 (filial generation 1) offspring were used to conduct linkage map-based QTL analysis. Markers for the construction of the genetic map were screened using the same scheme as above and stricter filter criteria (genotype deletion rate≤0.2, MAF (Minimum Allele Frequency)≥ 0.05) . . . . R/qtl software was used for QTL (quantitative trait locus) localization. Scanone( ) and cim( ) functions in R/qtl were respectively used to perform interval mapping (IM) and composite interval mapping (CIM). The scan step was 1 cM, and other parameters were set to default values. For the threshold of the LOD score, each trait was permutated 1000 times, and a 5% confidence threshold was selected. Consecutive regions with LOD values larger than the threshold were called QTLs. For each QTL, the region with the highest LOD value was judged as the peak of this QTL. If the distance between peaks of two adjacent QTLs was <10 cM, then the QTLs were merged by the define.peak ( ) function in the R package eqtl. The boundary of each QTL was determined by 1.5-LOD drop support intervals. This method refers to the define.peak( ) function of the eqtl software package.

2.4 Further Narrow the Range of QTL Interval

The mutation information related to the target region in QTL-seq analysis was used, the Kompetitive Allele Specific PCR (KASP) was used to determine the marker for precisely location. A total of 10 KASP markers were designed to genotype 328 individuals, including 8 parental individuals and 320 F1 (filial generation 1) Color-sectored Monospore Developed individuals.

2.5 RNA-Seq

For gene expression analysis in candidate regions, RNA-seq sampling was performed on leaves from two parents with the same living conditions. Three biological replicates were performed for each parent sampling. The total RNA was extracted by the plant RNA kit (OMEGA), and the first strand cDNA was prepared by the HiScript II Q RT SuperMix (Vazyme Biotech) for the qPCR kit. RNA Nano 6000 analysis kit and Bioanalyzer 2100 system (Agilent Technologies) were used to evaluate RNA quality. Sequencing libraries were generated using VAHTS Total RNA-Seq Library Prep Kit (Vazyme Biotech). Then the libraries were pair-end sequenced on an Illumina HiSeq 2000 platform (Illumina, USA) with the read length of 150 bp.

The quality of raw sequencing reads were evaluated by FastQC and Trimmomatic. Differential gene and transcript expression were analyzed by TopHat and Cufflinks.

3 Results 3.1 QTL-Seq

Figure 2:
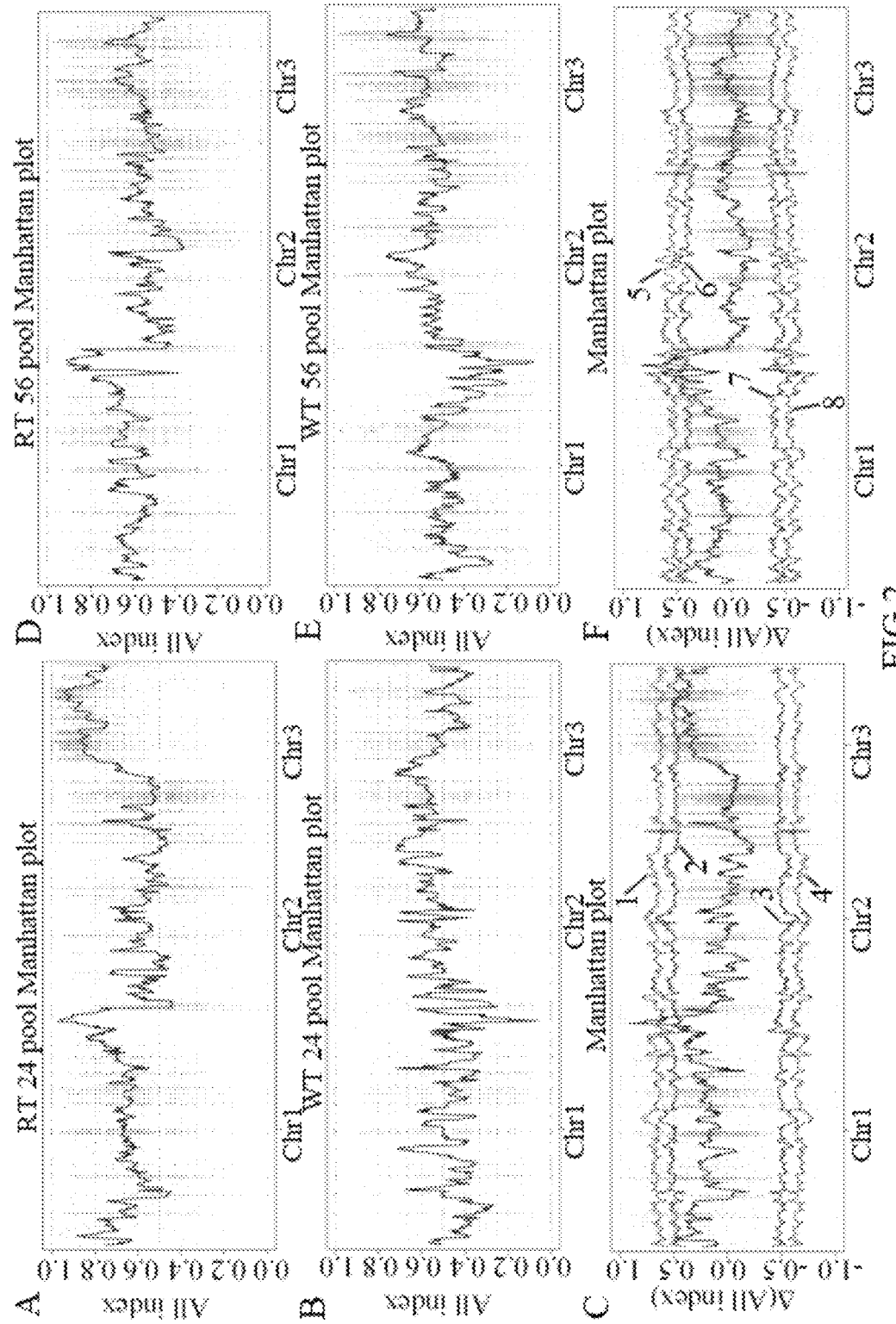
FIG. 2 is a Manhattan plot of two pairs of All-index and Δ(All-index) containing different numbers of individuals (the abscissa is the physical location of the Chromosome, and the ordinate is Δ(All-index), A-C: each offspring mixed pool contains 24 individuals, D-F: each offspring mixed pool contains 56 individuals; The pair of outer lines (1 and 4) of C in FIG. 2 indicated statistical confidence intervals under the null hypothesis of no QTL (P<0.01) and the pair of inner lines (2 and 3) of C in FIG. 2 indicated statistical confidence intervals under the null hypothesis of no QTL (P<0.05); The pair of outer lines (5 and 8) of F in FIG. 2 indicated statistical confidence intervals under the null hypothesis of no QTL (P<0.01) and the pair of inner lines (6 and 7) of F in FIG. 2 indicated statistical confidence intervals under the null hypothesis of no QTL (P<0.05).
Figure 3:
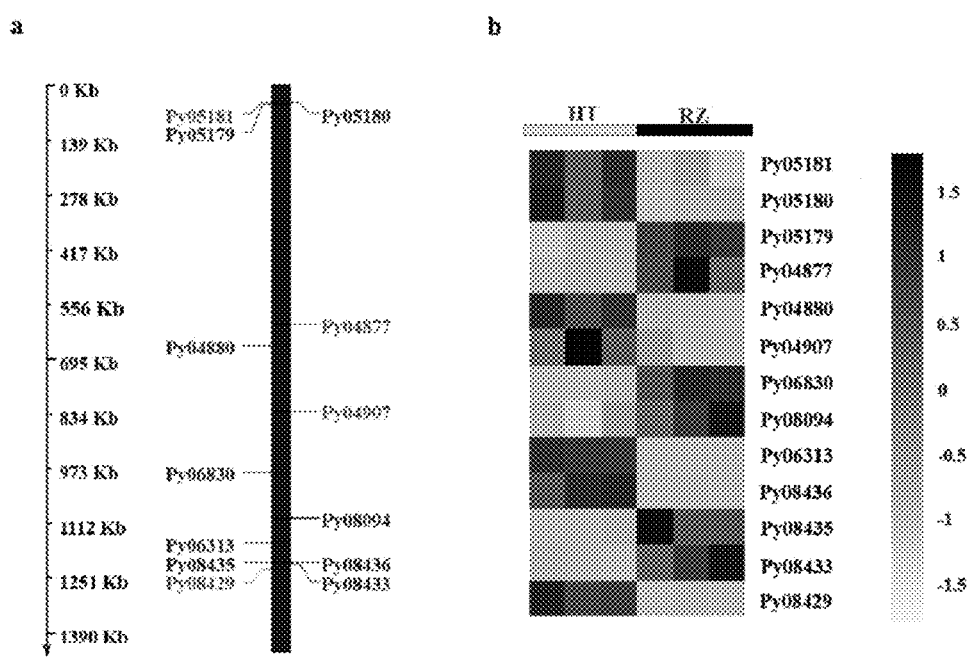
FIG. 3 is a thermography of the distribution and expression pattern of 13 differentially expressed genes (DEG) in the 1.42 Mb target region, wherein a is the distribution of 13 differentially expressed genes (DEG) in the 1.42 Mb target region; b is a heatmap of the expression pattern of 13 differentially expressed genes (DEG) in the target region.

By resequencing the five genomic libraries from the pools, including the HT and four offspring mixed pools, a total of 133.4 Gb was generate. The sequencing sequences of five DNA libraries are aligned to the RZ reference genome, and SNP sites and InDels are detected. A total of 24,159 SNP/InDels that occurred in HT and not in RZ were considered in calculating the SNP/InDel-index (All-index), and Δ(All-index) is calculated based on the All-index of the RT mixed pool and the WT mixed pool (FIG. 2). If it is a genomic region containing the target gene, its Δ(All-index) value should be significantly different from 0. For the RT24 and WT24 pools, the four regions are significantly different from 0 at the 95% significance level, and their total span length is 7.9 Mb (Table 1). For the RT56 and WT56 pools, only the two regions at the terminal of chromosome 1 are significantly different from 0, and their total span length is 4.9 Mb (Table 1). These results show that the mixed pool with more individuals has a better locating function, and it is recommended to use a mixed pool with a number of ≥50 individuals for location of traits. Specifically, in present experiment, since the combination of two sets of mixed pool locating intervals can further narrow the candidate interval, in this experiment, the candidate region of the red locus (rcl-1) is determined on chromosome 1 from 39,700,001 to 43,000,000 based on the results of the two-pair locating. (Table 1).

TABLE 1

The candidate regions identified by QTL-seq

| Pools-pair | Candidate regions (95% significance level) | Overlapping region |
|---|---|---|
| RT24-WT24 | 1,400,001-2,700,000 on chromosome 1<br>39,600,001-43,200,000 on chromosome 1<br>21,900,001-23,900,000 on chromosome 3<br>27,000,001-28,000,000 on chromosome 3 | 39,700,001-43,000,000 on chromosome 1 |
| RT56-WT56 | 36,400,001-38,000,000 on chromosome 1<br>39,700,001-43,000,000 on chromosome 1 | |

3.2 Verification of Candidate Region 86 of Color-sectored Monospore Developed individuals from RZ×HT is used to further confirm the 39,700,001-43,000,000 region on chromosome 1. A total of 17,888 makers are screened to construct a genetic map, and then the co-segregated makers are gathered into recombined bin makers. Finally, a total of 243 recombined bin makers are actually used to construct the genetic map. The map is composed of 3 chromosomes, covering 472.45 CM, and the average distance is 1.94 cM. The R/qtl software package is used for QTL (quantitative trait locus) analysis of red and wild-type traits. The QTL (quantitative trait locus) interval between Marker4105 and Marker4115 located near the QTL-seq candidate region is identified on chromosome 1. Marker4105 and Marker4115 are 3.57 cM apart, which corresponds to a physical distance of 2.74 Mb (based on the RZ genome sequence of *Pyropia yezoensis*, located in the region 40,839,807-43,583,607 on chromosome 1), which overlaps the region identified by QTL-seq. The results of traditional QTL (quantitative trait locus) analysis proved the accuracy of QTL-seq locating results.

3.3 KASP Further Narrows the Candidate Interval

There are 36 high-quality SNP/Indel sites in the candidate regions identified by QTL-seq. In order to further narrow the scope of the candidate interval, 10 of KASP markers are developed, and finally 4 of them (SNP1-4) are determined to use to genotype 328 samples. Among these samples, recombination events are found at the SNP1 loci in 9 samples (F1-CMD-PWT14-2, F1-CMD-PWT2-2, F1-CMD-W12-1, F1-CMD-W21-3, F1-CMD-W22-1, F1-CMD-WT16, F1-CMD-WT33, F1-CMD-WT55, F1-CMD-WT81). Due to the high co-segregation strength, no recombination events are found in the other three loci. In this way, the candidate range of the red coloration locus is reduced to 1.42 Mb (41,578,129-43,000,000 on chromosome 1). Taking the RZ genome as a reference, 141 genes are annotated in the target region. Among the 27 SNPs identified in the final candidate region, 24 SNPs were located within the intergenic region; two SNPs were located in up/down regulatory region that was associated with Py04887, Py08429, and Py08430. Subsequent transcriptome analysis revealed that Py04887 and Py08430 did not exhibit significant changes in RZ and HT. Remarkably, only one non-synonymous SNP [A/C] in the coding region of Py08429 was located in the final candidate region.

3.4 RNA-Seq to Determine Candidate Genes

In order to further determine the candidate genes related to red coloring in *Pyropia yezoensis*, RNAseq analysis is performed on samples collected from two parents. A total of 1459 differentially expressed genes are detected (|log 2 (fold-change)|>1), including 605 annotated genes and 854 predicted novel genes. Compared with RZ, 718 of genes are up-regulated, while 741 of genes are down-regulated in HT. It should be noted that among these genes, compared with RZ, HT up-regulates a phycoerythrin (Py09239) y subunit gene (Py09239), which is directly related to pigment; the expression level of magnesium chelatase subunit H (Py02527) of the chlorophyll metabolism pathway in HT is lower than that in RZ. However, Py09239 and Py02527 are not included in the candidate interval in result 3.3, indicating that the causal gene may change the color of leaf by adjusting the change of pigment content.

In order to determine the potential candidate genes that controlling red coloring in HT, 141 of genes in the 1.42 Mb candidate interval are selected, and it is found that only 13 of genes showed a significant difference between RZ and HT (|log 2 (fold-change)|>1). Combining the information of interval variation in result 3.3, we can infer that a Py08429 gene that carries non-synonymous SNP (A/C) and was significantly up-regulated (>6-fold) in the red mutant HT is the candidate gene regulating red coloration in *P. yezoensis*.

We cloned Py08429 from RZ and HT. The results show that there is one exon, the predicted coding sequence (CDS) of the cloned Py08429 cDNA is 1338 bp, and the predicted corresponding protein length is 446 amino acids. The alignment of the Py08429 sequence between the wild-type and the red mutant shows that there is a non-synonymous A→C mutation in the exon, resulting in the conversion of the $331^{st}$ amino acid from glutamine (Gln, Q) to proline (Pro, P) at residues.

3.5 Verification of Candidate Gene

In order to study the conservation of the red mutant locus, 21 of different wild-type *Pyropia yezoensis* in the laboratory are randomly selected for PCR verification, and then subjected to Sanger sequencing. It is found that in this locus, the amino acid locus translated from 21 of wild-type *Pyropia yezoensis* are the same as the RZ protein locus. These findings indirectly indicate that Py08429 may be a candidate gene for regulating the red coloring of *Pyropia yezoensis*.

The above are only preferred embodiments of the present disclosure, and are not intended to limit the present disclosure in other forms. The present disclosure may be changed or modified into equivalent embodiments with equivalent changes by anyone familiar with the field. However, any simple modifications, equivalent changes and modifications made in the above embodiments based on the technical essence of the present disclosure without departing from the content of the present disclosure still belong to the protection scope of the present disclosure.

What is claimed is:

1. A method for rapid and accurate chromosomal location of traits in layer, comprising following steps: marking and distinguishing different genotype regions of thallus in layer developed from meiotic tetrad by color difference of pigment mutants, inducing and releasing monospores based on asexual reproduction of monochromatic single-genotype sectors of leaves for obtaining complete leaves with same genotype in batch, forming offspring Color-sectored Monospore Developed population to evaluate and measure a commonality of target genetic trait; using a genome of one of the wild-type parents as a reference genome and performing QTL-seq analysis on a collection of offspring exhibiting extreme phenotypes of offspring Color-sectored Monospore Developed population by SNP or #InDel markers; and combining Kompetitive Allele Specific PCR and RNA-seq methods to predict location of target trait genes or major QTL;

wherein the QTL-seq analysis comprising following steps:
i. in the offspring Color-sectored Monospore Developed population of hybrid of wild-type×pigment mutants, mixing a quantity of offspring Color-sectored Monospore Developed individuals according to their traits to form a pair of extreme trait offspring pool with same individual quantity;
ii. performing whole-genome sequencing of wild-type parents, pigment mutants and offspring pool; filtering sequenced data, calling and filtering SNP and/or InDels and annotating SNP and/or InDels;
iii. extracting SNP or InDels which are homogenic in each parent but different between two parents; using genotype of the wild-type parents as a reference to calculate Δ(SNP/InDel-index) of offspring pool; determining candidate genomic region related to mutant trait;
wherein number of individual quantity in each extreme trait offspring pool is ≥24;
analyzing wild-type pool and red mutant pool of the offspring Color-sectored Monospore Developed population of cross combination of wild-type RZ×red mutant HT by QTL-seq to locate red trait locus of layer leaf within 4.9 Mb; and
further narrowing candidate interval to 1.42 Mb by Kompetitive Allele Specific PCR; combining with RNA-seq method to determine potential candidate gene for controlling red coloring in HT is Pv08429.

2. The method for rapid and accurate chromosomal location of traits in layer according to claim 1, wherein comprising following steps:
filtering sequenced original sequence and annotating SNP and/or InDels said in the step ii as: marking repeats by Picard software; detecting single nucleotide polymorphism and InDels by SAMtools and GATK software; filtering standards of SNP or InDels are as follows: read depth ≥4, ≤1000; mapping quality ≥20; adjacent SNP distance ≥5 bp; annotating SNP or InDels by ANNOVER software.

3. The method for rapid and accurate chromosomal location of traits in layer according to claim 1, wherein the Δ(SNP/InDel-index) is difference between SNP or InDel-index of each SNP/InDel in one offspring mixed pool subtracts SNP/InDel-index of another mixed pool.

4. The method for rapid and accurate chromosomal location of traits in layer according to claim 1, wherein SNP/InDel-index comprising following steps:
extracting SNP or/InDels which are homogenic in each parent but different between the two parents; using the genotype of the wild-type parents as a reference to calculate ratio of number of reads of pigment-mutant parent mutation in offspring pool to total number respectively, which is SNP/InDel-index.

5. The method for location of traits according to claim 1, wherein forming the offspring Color-sectored Monospore Developed population comprising following steps:
i. crossing wild-type×pigment mutants to obtain Flof chimeric leaves, marking and distinguishing the different genotype regions of thallus in layer developed from meiotic tetrad on the chimeric leaves by color of pigment mutants, and each region is a single-genotype;
ii. inducing and releasing monospores by the asexual reproduction of single-genotype regions, sectioning single-genotype region into small pieces and cultivating at 15° C., to obtain numerous complete leaves with the single-genotype, forming offspring Color-sectored Monospore Developed population to measure and analyze genetic trait.

6. The method for location of traits according to claim 1, wherein comprising following steps:
filtering sequenced data, calling and filtering SNP and/or InDels and annotating SNP and/or InDels said in the step ii as: marking repeats by Picard software; detecting single nucleotide polymorphism and InDels by SAMtools and GATK software; filtering standards of SNP or InDels are as follows: read depth ≥4, ≤1000; mapping quality ≥20; adjacent SNP distance ≥5 bp; annotating SNP or InDels by ANNOVER software.

7. The method for location of traits according to claim 1, wherein Δ(SNP/InDel-index) is difference between SNP/InDel-index of each SNP or InDel in one offspring mixed pool subtracts SNP/InDel-index of another mixed pool.

8. The method for location of traits according to claim 1, wherein SNP/InDel-index comprising following steps:
extracting SNP or/InDels which are homogenic in each parent but different between two parents; using genotype of the wild-type parents as a reference to calculate ratio of number of reads of pigment-mutant parent mutation in offspring pool to total number respectively, which is SNP/InDel-index.

9. The method for rapid and accurate chromosomal location of traits in layer according to claim 1, wherein applications of method comprising species with haploid genotype chimeric characteristics.

* * * * *